United States Patent [19]

Martin et al.

[11] Patent Number: 5,578,286
[45] Date of Patent: Nov. 26, 1996

[54] TWO POWDER SYNTHESIS OF HYDROTALCITE-LIKE COMPOUNDS WITH DIVALENT OR POLYVALENT ORGANIC ANIONS

[75] Inventors: Edward S. Martin, New Kensington; John M. Stinson, Murrysville; Vito Cedro, III, Export; William E. Horn, Jr., Gibsonia, all of Pa.

[73] Assignee: Aluminum Company of America, Pittsburgh, Pa.

[21] Appl. No.: 482,390

[22] Filed: Jun. 7, 1995

Related U.S. Application Data

[63] Continuation-in-part of Ser. No. 290,220, Aug. 15, 1994, abandoned, which is a continuation-in-part of Ser. No. 235,504, Apr. 29, 1994, Pat. No. 5,514,361.

[51] Int. Cl.⁶ .............................. C07F 11/00; C07F 13/00
[52] U.S. Cl. .................. 423/593; 423/306; 423/367; 423/395; 423/420.2; 423/463; 423/556; 423/557; 423/558; 423/594; 423/595; 423/599; 423/600; 534/15; 534/16; 556/1; 556/13; 556/15; 556/16; 556/19; 556/43; 556/44; 556/46; 556/49; 556/58; 556/61; 556/62; 556/87; 556/90; 556/112; 556/114; 556/121; 556/131; 556/140; 556/147

[58] Field of Search .................. 423/420.2, 593, 423/306, 367, 395, 463, 556, 557, 558, 594, 595, 599, 600; 534/15, 16; 556/1, 13, 15, 16, 19, 43, 44, 46, 49, 58, 61, 62, 87, 90, 112, 114, 121, 131, 140, 147

[56] References Cited

U.S. PATENT DOCUMENTS 5,399,329  3/1995  Schutz et al. .................. 423/415.1

*Primary Examiner*—Wayne Langel
*Attorney, Agent, or Firm*—Gary P. Topolosky

[57] ABSTRACT

There is provided a method for making a divalent or polyvalent organic anion-intercalated hydrotalcite-like materials by first reacting a magnesium-containing powder and a transition alumina powder in an aqueous suspension to form a meixnerite intermediate. This intermediate is then contacted with a dicarboxylate or polycarboxylate anion to form a hydrotalcite-like material. The latter is then separated from the suspension. Representative materials include an oxalate-, succinate- or terephthalate-intercalated hydrotalcite-like material.

47 Claims, No Drawings

TWO POWDER SYNTHESIS OF HYDROTALCITE-LIKE COMPOUNDS WITH DIVALENT OR POLYVALENT ORGANIC ANIONS

This application is a continuation-in-part and divisional of U.S. application Ser. No. 08/290,220, filed on Aug. 15, 1994, abandoned which is a continuation-in-part of U.S. application Ser. No. 08/235,504, filed on Apr. 29, 1994, U.S. Pat. No. 5,514,361 both disclosures of which are fully incorporated by reference herein.

BACKGROUND OF THE INVENTION

1. Field of the Invention

This invention relates to the field of making mixed metal hydroxides or layered double hydroxide products. More specifically, the invention relates to an improved two-step method for making hydrotalcite and hydrotalcite-like compounds from dry powder constituents.

2. Technology Review

Hydrotalcite exists in both a natural and synthetic form. Naturally occurring deposits have been found in Snarum, Norway and in the Ural Mountains. Typical occurrences are in the form of serpentines, talc schists, or as an alteration product where hydrotalcite forms the pseudomorph of a spinel. Like most ores, natural hydrotalcite is virtually impossible to find in a pure state. Such deposits often contain one or more other minerals including penninite and muscovite.

Several methods are known for making synthetic hydrotalcite in such product forms as a fine powder, −20 mesh granules or as ⅛-inch diameter extrudates. One representative method is described in U.S. Pat. No. 3,539,306. There, an aluminum hydroxide, aluminum-amino acid salt, aluminum alcoholate, water soluble aluminate, aluminum nitrate and/or aluminum sulfate are mixed with a magnesium component selected from magnesium oxide, magnesium hydroxide or water-soluble magnesium salt and a carbonate ion-containing compound in an aqueous medium maintained at a pH of 8 or more. The resulting product may be used as a stomach antacid. In this typical neutralization process, a fairly pure, finely sized hydrotalcite particle is formed. A serious disadvantage of this method, however, is its formation of a sodium salt by-product. This salt neutralization process for making hydrotalcites could also produce a brucite-like structure with undesired anions (e.g. sulfate) or cations ($Na^+$) included therein.

In Misra Reissue U.S. Pat. No. 34,164, the disclosure of which is fully incorporated by reference, yet another means for synthesizing hydrotalcite is taught. The method comprises heating magnesium carbonate and/or magnesium hydroxide to form activated magnesia, then combining the activated magnesia with an aqueous solution of aluminate, carbonate and hydroxyl ions.

Other known methods for synthesizing hydrotalcite include: adding dry ice or ammonium carbonate to a thermal decomposition product from a magnesium nitrate–aluminum nitrate mixture, after which intermediate product is subjected to temperatures below about 325° F. and pressures of 2,000 to 20,000 psi. Yet another process, from "Properties of a Synthetic Magnesium-Aluminum Carbonate Hydroxide and its Relationship to Magnesium-Aluminum Double Hydroxide Manasseite, and Hydrotalcite", *The American Mineralogist*, Vol. 52, pp. 1036–1047 (1967), produces hydrotalcite-like materials by titrating a solution of $MgCl_2$ and $AlCl_2$ with NaOH in a carbon dioxide-free system. This suspension is dialyzed for 30 days at 60° C. to form a hydrated Mg-Al carbonate hydroxide having the properties of both manasseite and hydrotalcite.

It is a principal objective of this invention to provide an improved means for making synthetic hydrotalcite and hydrotalcite-like compounds from two or more relatively inexpensive, dry powder components. It is another objective to provide an improved process for making hydrotalcite and related materials with less sodium ion contamination. It is still another objective to provide a method for synthesizing hydrotalcite without depending on the use of any alumina gels. It is still another objective to make hydrotalcite and hydrotalcite-like compounds through the further processing of an improved meixnerite product, itself made by combining activated magnesia with a high surface area, transition alumina.

Yet another principal objective is to make hydrotalcite and hydrotalcite-like compounds in a more environmentally acceptable manner. According to preferred embodiments, the synthetic hydrotalcites made by the methods described hereinbelow yield no by-products other than water. Any remaining discharge waters should be easily disposable due to their low dissolved solids content.

SUMMARY OF THE INVENTION

In accordance with the foregoing objectives and advantages, there is provided an improved method for making dicarboxylate or polycarboxylate anion-intercalated, hydrotalcite-like materials by first reacting a magnesium-containing powder and a transition alumina powder in an aqueous suspension to form a meixnerite intermediate. This intermediate is then contacted with a dicarboxylate or polycarboxylate anion to form a hydrotalcite-like material. The latter is then separated from the suspension. Representative materials include an oxalate-, succinate- or terephthalate-intercalated hydrotalcite-like material.

The foregoing stems from an alternate means of making synthetic hydrotalcite. The method comprises reacting powdered magnesium oxide with a high surface area, transition alumina in a suspension or slurry to form meixnerite or a meixnerite-like intermediate. The latter intermediate is then contacted with an anion source such as an acid or acid precursor, most preferably carbon dioxide, to form the layered double hydroxide compound which is separated from the suspension by filtering, centrifugation, vacuum dehydration or other known means. On a preferred basis, the transition alumina so combined with activated magnesia consists essentially of an activated alumina powder having a surface area of about 100 $m^2/g$ or greater. For related double hydroxide formations, still other reactants, such as bromides, chlorides, boric acids, or their salts, are combined with the meixnerite intermediate to make similarly structured, brucite-like layered double hydroxide family members.

Still another principal objective of this invention is to make hydrotalcite or hydrotalcite-like materials which have a greater degree of variation in the magnesium to aluminum ratios thereof. Another principal objective is to provide hydrotalcite-like family members with different divalent and trivalent anion substitutes than magnesium and aluminum, respectively. Yet another main objective is to provide hydrotalcites and hydrotalcite-like materials which have intercalated into their structure by the method of this invention one or more of the following materials: a monovalent inorganic anion, divalent inorganic anion, polyvalent inorganic anion, monovalent organic anion, and a divalent or polyvalent organic anion.

DETAILED DESCRIPTION OF PREFERRED EMBODIMENTS

1. Definitions

As used herein, the following terms shall have the meanings provided hereinbelow:

a. "Transition alumina" means a high surface area alumina in a powdered or fine particulate form. One preferred way of defining such alumina materials uses surface area and Loss on Ignition (LOI) measurements, the latter being defined as the weight lost on heating dry material from about 110° to 1100° C. More specifically, an alumina having a Brunauer-Emmett-Teller [or B.E.T.] measured surface area of about 100 m$^2$/g or more would be considered as having a high surface area and thus qualify as a transition alumina for purposes of this invention. Aluminas having an LOI weight percentage of about 15% or less would also qualify under this definition.

One particular preferred type of transition aluminas is referred to as a "rehydratable alumina". It tends to form strong hydroxyl bonds on contact with water and its rehydration reactions are highly exothermic. The average particle sizes for such aluminas may range from 0.01–200μ, with a range of about 0.1 to 10 or 20 micrometers being more preferred.

Certain activated aluminas are more suitable than others for purposes of this invention. Most are high surface area aluminas formed by the rapid calcination of hydrated alumina at temperatures below that required for complete dehydration or calcination. Typically, such aluminas are amorphous (i.e., have no microcrystalline structure) as determined by X-ray diffraction. These powders exhibit an LOI value of about 4–12% by weight, a B.E.T. surface area of about 100–300 m$^2$/g, or both properties.

b. "Activated magnesia" or activated magnesium oxide refers to the magnesium-based product activated by "soft burning" MgO at one or more temperatures between about 450° and 900° C. This component has a general surface area of about 10–200 m$^2$/g, preferably about 20–150 m$^2$/g and an LOI ranging from 1.0 to 6.0 wt. %. Such criteria distinguishes this reactant from magnesias which have been dead-burned or completely calcined. Although the latter may still produce meixnerite with longer reaction times or under more strenuous reaction conditions, the percent yields from such conditions are significantly lower than those preferred for the present invention.

There are numerous means for making an activated magnesia product to combine with transition aluminas according to the first method step of this invention. For example, commercially sold magnesium carbonate can be heated to drive off carbon dioxide and thus form a reactive magnesia thereby. Magnesium oxide may also be made by: (a) heating natural or synthetic magnesium hydroxides or basic magnesium carbonate, to temperatures between about 380° and 950° C.: or (b) by heating MgCl$_2$ with lime. Various known methods may be used to generate magnesia powders of various particles sizes and/or surface areas.

c. "Hydrotalcite" compounds shall be understood to apply to the structural family of layered double hydroxides whose family members consist of any compound having the formula: $A_{1-x}B_x(OH)_2C_z.mH_2O$, where A represents a divalent metal cation, B represents a trivalent metal cation, C represents a mono- to polyvalent anion, and x, z and m satisfy the following conditions: $0.09<x<0.67$; $z=x/n$, where n=the charge on the anion; and $2>m>0.5$. When converting to whole numbers rather than fractional equivalents, preferred embodiments of this family have also been identified by the formula: $A_6B_2(OH)_{16}C_z.4H_2O$, wherein A is selected from: $Mg^{2+}$, $Ni^{2+}$, $Cu^{2+}$, $Ca^{2+}$, $Fe^{2+}$, $Co^{2+}$, $Sn^{2+}$, $Mn^{2+}$, $Cr^{2+}$, $Cd^{2+}$, $V^{2+}$ and $Zn^{2+}$; B from: $Al^{3+}$, $Fe^{3+}$, $Ga^{3+}$, $Co^{3+}$, $Mn^{3+}$, $Sc^{3+}$ and $Cr^{3+}$; and C from an anion list which includes: $OH^-$, $Cl^-$, $Br^-$, $NO_3^-$, $CH_3COO^-$, $CO_3^{2-}$, $SO_4^{2-}$, $PO_4^{3-}$, $Fe(CN)_6^{3-}$, $Fe(CN)_6^{4-}$ and some borates, carboxylates and polyoxometallates among other monovalent, divalent, and polyvalent inorganic and organic anions.

Some references refer to any compound having the aforementioned formulae as "hydrotalcite". For purposes of this invention, however, this family of structural compounds has been divided into various subgroups depending on the divalent and trivalent cations within its alternating brucite-like layers. For example, pyroaurites have the basic formula: $Mg_6Fe_2(OH)_6CO_3.4H_2O$. Such compounds are also known as "sjogrenites". Collectively, these other family members have been referred to as "hydrotalcite-like" compounds.

Yet another preferred definition for the term "hydrotalcite" includes any natural or synthetic compound satisfying the general formula: $Mg_{1-x}Al_x(OH)_2(CO_3)x_{/2}.mH_2O$. In its ionic form, hydrotalcite may appear as: $[Mg_{1-x}Al_x(OH)_2]^+x.[(CO_3)x_{/2}]^{-x}.mH_2O$. This compound has also been written sometimes as: $6MgO.Al_2O_3.CO_2.12H_2O$. The main structural unit for this compound is brucite, or magnesium hydroxide ($Mg(OH)_2$) having the form of an octagonal sheet with Mg ions positioned between multiple (OH) ions which share adjacent edges. By substituting trivalent aluminum ions for some of the divalent magnesium of this structure, sublayers of magnesium and aluminum are created while still maintaining brucite's basic sheet-like structure. To compensate for the charge imbalance from these aluminum ion substitutions, anions (indicated by letter "C" in the foregoing formulae) and water molecules are intercalated therein to form interlayers of ($C_z.mH_2O$) between the brucite-like structural layers, with $z=x/n$, where n=charge of the anion intercalated. The anion having the greatest affinity to combine with water in this structure and form hydrotalcite is carbonate ($CO_3^{2-}$). Sulfate ($SO_4^{2-}$) is another compatible anion. Yet in other embodiments, a range of other materials may be intercalated into hydrotalcite's basic structure according to this invention. For instance, the "C" of the foregoing formula may also be one or more of the following groups of anions: $OH^-$, $Cl^-$, $Br^-$, $NO_3^-$, $CH_3COO^-$, $PO_4^{3-}$, $Fe(CN)_6^{3-}$, $Fe(CN)_6^{4-}$ and some borates carboxylates and polyoxometallates among other monovalent, divalent, and polyvalent inorganic anions and monovalent organic, dicarboxylate or polycarboxylate anions.

The spacial distribution of carbonate ions within hydrotalcite partially depends on how the $Al^{3+}$ ions substitute for the $Mg^{2+}$ ions therein. Brucite layer spacing is also a function of the amount or degree of aluminum substitution into hydrotalcite's basic structure. As aluminum substitution increases, interlayer spacing decreases due to an increase in the electrostatic attraction between positive hydroxide layers and hydrotalcite's negative interlayers. Interlayer thicknesses may also vary depending on the size and orientation of the anions substituted for some or all of the carbonate ions in hydrotalcite.

From preferred embodiments, a hydrotalcite material is contemplated having a Mg:Al ratio ranging from about 2:1 to about 3:1 or higher (or, when expressed fractionally from about x=0.33 to about x=0.25, respectively). It is to be understood, however, that a variety of hydrotalcites may be made hereby, with Mg:Al ratios also ranging from about 0.5:1 to about 10:1, (or for x values equal from about 0.67 to about 0.091).

d. "Basic magnesium carbonate" means a dimagnesium salt containing hydroxide and carbonate anions in the same powder product, sometimes represented by the formula $Mg(OH)_2 \cdot MgCO_3$.

e. "Meixnerite" means a hydrotalcite-like, layered double hydroxide material in which all the intercalated anions are hydroxyls.

f. "Monovalent inorganic anions" means those monovalent anions appropriate for incorporation into a basic meixnerite compound according to this invention and include: representative monoatomic anions such as chloride, diatomic species such as cyanide, and polyatomic species such as nitrate and thiocyanate. These anions can be generically designated $A^-$ and supplied to the reactions described herein as an acid (HA), or acid precursor such as the reaction product of an acid with a base like sodium hydroxide, potassium hydroxide, ammonium hydroxide, calcium oxide, magnesium carbonate and the like, (or $MA_x$, where x=the valency of the cation M). This acid precursor can also be the ammonium or substituted ammonium salt of the acid, RR'R"HNA, where R, R' and R" can independently=H or a short chain hydrocarbyl moiety such as methyl, ethyl, etc. Preferred sources for such anions are the acids, and their sodium, potassium or ammonium salts. For still other anion intercalates herein, an acid anhydride is the appropriate anion delivery form.

Examples of the monovalent inorganic anions possible to be incorporated into a basic hydrotalcite-like structure by this invention include: chlorides, bromides, nitrates, cyanides, bicarbonates, bisulfates, chlorates, hypochlorites, iodates, iodides, metaborates, nitrites, perborates, perchlorates, periodates, monobasic phosphates, tetrafluoroborates, vanadates, perrhenates, thiocyanates, permanganates, niobates (V), tantalates (V), aluminates, hexahydroxyantimonates, bismuthates and the like.

g. "Divalent inorganic anions" means those divalent anions appropriate for incorporation into a basic hydrotalcite-like material according to this invention and include representative monoatomic species such as sulfides, and polyatomic species such as sulfates, chromates, tetracyanonickelates and the like. These anions can be supplied to the process as the acid, acid salt or ammonium salt. These can be represented as: $H_2A$ or $M_2A$, where M=a monovalent cation; MA, where M=a divalent cation; and $(NRR'R"H)_2A$, where R,R' and R"=H or a short chain hydrocarbyl moiety. The M is preferably an alkali or alkaline earth metal such as lithium, sodium or magnesium. Suitable divalent inorganic anions for intercalation into a hydrotalcite-like material by this invention include: sulfates, metasilicates, persulfates, dibasic phosphates, selenates, sulfides, sulfites, tellurites, tetraborates, thiosulfates, trisilicates, dichromates, molybdates (VI), hexachloroiridates (IV), hexachloropalladates (IV), hexachloroplatinates (IV), ferricdisulfates, tetrachloropalladates (II), tetrathiotungstates, tungstates (VI), dichromates, metavanadates, dimolybdates, chromates, tetrachlorocuprates (II), tetracyanonickelates, stannates, arsenates, selenites, silicates, tellurates, and the like.

h. "Polyvalent inorganic anions" means those polyvalent anions appropriate for incorporation into a basic hydrotalcite-like material according to this invention. Such anions can be supplied via their acid, ammonium salt or anhydride forms and generally described as: $H_xA_{(x-)}$, where x indicates the negative charge on the anionic species; $M_xA_{(x-)}$, where M has a +1 valence; $M^{(y+)}{}_xA^{(x-)}{}_y$, where M and A are polyvalent and where y is the charge on the cation and x the charge on the anion, and where M can be an alkali or alkaline earth metal or an RR'R"HN, where R, R' and R" can be H or a short chain hydrocarbyl moiety. Suitable polyvalent inorganic anions for this invention include: phosphates (3⁻), pyrophosphates (4⁻), borates (3⁻), hexanitrocobaltates (III, 3⁻), ferricyanides (3⁻), ferrocyanides (4⁻), pyrophosphates (4⁻), metatungstates ($W_{12}O_{39}$,6⁻), paramolybdates ($Mo_7O_{24}$,6⁻), polyphosphates and the like.

i. "Monovalent organic anions" means those monovalent anions appropriate for incorporation into a hydrotalcite-like material according to this invention. Such anions can be represented by the general formula RCOO— where R can be hydrogen, an alkyl, substituted alkyl, alkenyl, substituted alkenyl, aryl or substituted aryl moiety. "Alkyl" includes hydrocarbyl species from C1 to about C30 which can be straight chains or contain branched hydrocarbon chains. "Substituted alkyl" groups can contain from C1 to about C30 carbon atoms and be substituted with halogen, hydroxyl, nitro, amino, sulfonyl, keto, sulfo, sulfono, phospho, phosphono, aryl and the like as substituent groupings. "Alkenyl" includes branched and unbranched carbon chains of C1 to about C30 and contain one or more double bonds. "Substituted alkenyl" can be substituted with hydroxyl, amino, nitro, keto, sulfo, sulfonyl, phospho, halogen, phosphono, aryl and the like as pendant groupings. "Aryl" includes aromatic hydrocarbons containing from 6 to 30 ring and substituent carbon atoms. These can be substituted with hydroxyl, halogen, amino, nitro, sulfonyl, phosphonyl, silyl and the like as substituent groupings. Pendant hydrocarbyl chains may contain these and other groups such as keto, sulfo, phospho and silo groups. Suitable carboxylic anions include: acetates, chloroacetates, dichloroacetates, trichloroacetates, bromoacetates, benzoates, 4-hydroxybenzoates, 4-bromobenzoates, 3-methylbenzoates, 3-phenylbenzoates, 1-naphthoates, 2-naphthoates, formates, propionates, butyrates, pentanoates, hexanoates, octoates, 2-ethylhexanoates, decanates, dodecanoates, stearates, octadecanoates, palmitates, acrylates, 2-butenoates, behenoates, cinnamates, lactates, methacrylates, glycolates, salicylates, 3,5-dihydroxybenzoates, rincinoleoates, anisates, 3-chloropropanoates, 3-nitrobenzoates, oleoates, linolenoates, aminoacetates, cyclohexanoates, levulinoates, pyruvoates and the like.

j. "Divalent and polyvalent organic anions" mean those anions appropriate for incorporation into a hydrotalcite-like material according to this invention. Such anions can be represented by the general formula $R(COO^-{}_x)$, where x=2 or greater. R can be nil, an alkyl from C1 to about C30, an alkenyl from C2 to about C30, or an aryl from C6 to about C30. All of these anions can contain straight or branched chains. Alkenyl anions contain at least one double bond but can contain more than one in either a straight or branched chain. The aryl anions contain at least one aromatic group. All of these may be substituted with: a halogen, nitro, amino, hydroxyl, sulfo, sulfonyl, phosphono, phophonyl, sulfuryl, alkoxyl, or keto grouping. Suitable forms of these organic anions include: the acid; its alkali or alkaline earth salts; the ammonium salts; $(RR'R"HN)_xA$, where R, R', R"=H or a short chain hydrocarbyl moiety and x=the anionic charge of the anion, the acid anhydrides; (HOOC)R(CO)O(CO)R, (COOH); the esters; $R(COOR')_x$ and the like. Examples of the divalent and polyvalent organic anions useful in this invention include: oxalates, malonates, succinates, glutarates, adipates, pimelates, suberates, sebacates, decandioates, dodecandioates, maleates, fumarates, tartrates, citrates, phthalates, isophthalates, terephthalates, 1,2,3-propanetricarboxylates, hemimellitates, 1,8-naphthalates, pyromellitates, diphenates, saccharates, tetrabromophthalates, and the like.

One generic means for summarizing the reactions believed to occur by the method described herein is as follows:

Step 1. $M^{+2}{}_aO_b+M^{+3}{}_cO_d.gH_2O \Rightarrow$ Meixnerite-like intermediate, then Step 2. Meixnerite-like intermediate+RA $\Rightarrow$ Layered Double Hydroxide+$H_2O$.

On a more preferred basis, the following two steps are believed to occur for hydrotalcite manufacture:

Step 1: $(1-x)MgO+x/2Al_2O_3+(1+x/2+w)H_2O \Rightarrow [Mg_{(1-x)}Al_x(OH)_2](OH)_x.wH_2O$, then Step 2: $2[Mg_{(1-x)}Al_x(OH)_2](OH)_x.wH_2O+x/2CO_2 \Rightarrow 2[Mg_{(1-x)}Al_x(OH)_2](CO_3{}^{2-})_{x/2}.wH_2O+xH_2O$.

For some dry powder reactants, temperature limitations on the contacting water solution have proven beneficial to overall yield. While Step 1 of the foregoing reaction may proceed at temperatures as low as 25° C. for calcium-containing compounds, even as low as 10° C. for still other calcium-related reactions, they usually proceed best at one or more temperatures between about 80° and 160° C. for most non-calcium related reactions, especially those for making magnesium-containing, layered double hydroxides by the method of this invention. At such temperatures, yields in excess of about 75% are commonly observed. More preferred reaction temperatures generally run between about 98° and 150° C. Though higher reaction pressures, up to about 8 atmospheres (or atm), have been known to enhance the synthesis of hydrotalcite and hydrotalcite-like compounds according to this invention, more preferred reaction pressures are usually between ambient and 4.7 atms, as determined by the vapor pressure of water.

Suitable end uses for the hydrotalcite products made by this method include acid neutralizers and scavengers, especially for polypropylene and polyethylene manufacturers, adsorbents for heavy metal anions from waste waters, stabilizing components for other polymer systems such as poly (vinyl chloride), flame retarders, smoke suppressers, catalysts, catalyst supports and viscosity control agents.

For some of the alternate embodiments, a generic description entails treating a preformed meixnerite intermediate or "precursor", as made by the step (a) methods described herein, with an acid or acid precursor under controlled pH conditions to ensure that the reaction remains neutral or slightly basic. The term "acid" herein connotes a hydrogen cation associated with an anion, e.g., hydrogen bromide, nitric acid, boric acid, stearic acid, and the like. The term "acid precursor" indicates an acid derivative or salt that forms from the reaction of the acid with a base or other reactive material. Such precursors include salts such as sodium bromide, potassium sulfate, ammonium tungstate and the like. Other precursors include compounds which can easily hydrolyze to the acid or acid anion under reaction conditions. Such materials include acid esters, acid anhydrides, acid amides and imides, acid, aryl or alkly chlorides, sulfates, nitrates, phosphates and the like. Urea and substituted ureas, and substituted carbonates are precursors to carbonic acid.

The main processes envisioned herein produce substituted or intercalated, hydrotalcite-like, layered double hydroxides by preparing meixnerite-like intermediate materials, then reacting that intermediate with an acid or acid precursor. This meixnerite-like material can be prepared and reacted in situ, or it can be isolated and reslurried in water or another reaction media. The acid or acid precursor can then be added as received, in an aqueous solution, as a solution in organic solvents, or as a solution from aqueous organic mixtures. This acid, or precursor, is preferably added at a controlled rate to maintain pH's above about 6.5 to 8.0. Appropriate organic solvents must be miscible with water and include such alcohols as ethanol, ethylene glycol, glycerol and the like. For this reaction, however, ketonic solvents, esters and acids cannot be used as solvents.

Further features, objects and advantages of the present invention will be made clearer from the detailed description of examples which follows. It is to be understood, however, that such examples are merely representative of this invention and should not be used to limit its scope in any manner.

EXAMPLES 1–7

Each of the following were conducted using a 1.8 liter capacity, internally stirred reactor charged with 750 ml of deionized water. In each case, after the respective divalent and trivalent metal compounds were added to the water and dispersed therethrough with continuous stirring, carbon dioxide was bubbled into the reactor from a pressurized cylinder. When respective reaction times were completed, the reactor was allowed to cool and excess carbon dioxide gradually vented into the atmosphere. The resulting slurry was then vacuum filtered using a Buchner funnel and a sample of each filtrate was further dried under vacuum before x-ray diffraction analyses were conducted thereon to determine which crystal phases were present in these dried solids.

COMPARATIVE EXAMPLE 1

100 grams of hydromagnesite having the formula $Mg_5(CO_3)_4(OH)_2.4H_2O$ and 47 grams of ground aluminum trihydroxide having an average particle size of 10.0 μm were charged to the reactor. Carbon dioxide was added until the reactor pressure reached 34.3 atm. The reactor temperature was then maintained between 25°–26° C. for about 4 hours. Analysis of the dried solids removed from this reaction showed the presence of hydromagnesite and alumina as gibbsite but no hydrotalcite.

COMPARATIVE EXAMPLE 2

For this example, another 100 grams of hydromagnesite were charged with 41.7 grams of the same ground $Al(OH)_3$ as in Example 1. Liquid carbon dioxide was added until the reactor pressure reached 36.4 atm. The reactor temperature was then maintained between 48°–53° C. for about 4 hours. Analysis of the dried solids removed from this reaction again showed the presence of hydromagnesite and gibbsite but no hydrotalcite.

COMPARATIVE EXAMPLE 3

The same quantity of hydromagnesite and ground $Al(OH)_3$ used for Example 2 were again charged to a reactor for this Example. With 43.9 atm of carbon dioxide added, the reactor charged for 4 hours at 90° C. still showed no sign of hydrotalcite in the recovered solids.

EXAMPLE 4

For this Example, 100 grams of the same hydromagnesite as before were charged with 31.0 grams of a rehydratable alumina having an average particle size of 2.0 μm. The slurry was stirred at room temperature for 3 hours while enough liquid carbon dioxide was added to raise the overall reactor pressure to 40.1 atm. The whole system was then heated to 50° C. for 2 hours. The dried filter cake from this reaction was found to contain major amounts of hydrotalcite by x-ray diffraction analysis.

EXAMPLE 5

For this Example, 100 grams of the same hydromagnesite as before were charged with 38.7 grams of a pseudoboehmite sold by Vista Chemical Co. under the tradename Catapal® SB, said material consisting of 65 μm diameter agglomerates of 0.1 μm basic particles. Enough carbon dioxide was added to take overall reactor pressure to 42.5 atm. The system was then kept between 48°–52° C. for 4 hours. X-ray diffraction analysis of the resulting filter cake showed that major amounts of hydrotalcite were present.

EXAMPLE 6

The same quantities of hydromagnesite and pseudoboehmite used for Example 5 were again charged to a reactor for this Example. With 52.0 atm of carbon dioxide added, the reactor charged for 4 hours at 90° C. resulted in a filter cake which had major amounts of hydrotalcite present (by x-ray diffraction analysis).

EXAMPLE 7

The same quantities of hydromagnesite and rehydratable alumina used for Example 4 were again charged to a reactor, but for this Example no additional carbon dioxide was added thereto. The system was heated to 50° C. for 2 hours. The resulting filter cake was analyzed to contain major amounts of hydrotalcite as well. However, the degree of hydromagnesite conversion for Example 7 was less than in Example 4 based on a comparison of x-ray diffraction peak intensities for these products.

EXAMPLES 8–11

For each of these examples, about 70 grams of MgO and 45.6 grams of rehydratable alumina hydrate were mixed with 1200 ml of deionized water in a round-bottom flask to form a slurry. The slurry was then stirred and heated to atmospheric boiling. The area in the flask over the slurry was purged with nitrogen to prevent reaction with $CO_2$ from the air. After six (6) hours in the reactor, samples were removed and analyzed. Considerable meixnerite was found in these samples. After 22 hours at boiling, conversion was nearly complete. Several portions of this slurry were then cooled below 40° C. and treated with carbon dioxide gas or atmospheric air for converting the meixnerite to hydrotalcite. Samples removed from this slurry were analyzed and shown to contain major amounts of hydrotalcite. For Example 9, an oxalate was formed by adding oxalic acid to the meixnerite slurry at about 26°–30° C. A borate form of hydrotalcite was made by adding boric acid to the meixnerite slurry for Example 10 and a stearate form was made by contacting meixnerite with stearic acid per Example 11.

EXAMPLE 12

For this example, 728.8 grams MgO (sold under the tradename Elastomag 100) and 393.4 grams of activated alumina (sold by Alcoa under the name CP-5) were slurried with 11.4 liters of distilled water in an autoclave. The autoclave was purged with nitrogen gas during filling to displace any carbon dioxide therein. After filling, the nitrogen purge was ceased and the reactor sealed and heated to 100° C. After 24 hours, the autoclave was cooled to below 40° C. and the contents discharged into a vessel under a nitrogen gas blanket. The resulting slurry was split into 500 milliliter portions and sealed in plastic bottles under nitrogen atmosphere. The contents of one bottle was vacuum filtered under a nitrogen blanket and dried overnight in a vacuum oven at 100° C. The solids weight was 74.2 grams. An analysis of these solids showed molar ratios of: magnesium to aluminum (2.16), carbon to aluminum (0.065); and water to aluminum (5.95). Surface area was 36 $m^2$/gram. X-ray diffraction showed only one hydrotalcite-like phase (d(003) spacing=7.61 Å) with the diffraction pattern shown in Table A. The formula for this material was then computed to be: $Mg_{0.68}Al_{0.32}(OH)_2(CO_3^{-2})_{0.02}(OH^{-1})_{0.28} \cdot 0.89H_2O$.

TABLE A

Powder diffraction pattern of hydrotalcite-like material synthesized in Example 12

| d spacing (Å) | Relative Intensity |
|---|---|
| 7.61 | 100 |
| 3.82 | 50.5 |
| 2.58 | 20.0 |
| 2.30 | 10.2 |
| 1.94 | 7.8 |
| 1.74 | 1.1 |
| 1.64 | 0.9 |
| 1.52 | 12.9 |
| 1.49 | 11.4 |

EXAMPLE 13

A 500 milliliter portion of the slurry from above Example 12 was placed in a beaker with a continuous purge of nitrogen gas. A solution of nitric acid (18.9 milliliters added to 150 milliliters of distilled water) was then added dropwise to this slurry until a pH of approximately 8.0 was reached. The nitric acid addition was 10.54 grams and an equilibrium pH of 8.12 was measured. This slurry was vacuum filtered and the solids dried overnight in a vacuum oven at 100° C. The solids weight was 61.8 grams. An analysis of these solids showed molar ratios of: magnesium to aluminum (2.10); carbon to aluminum (0.062); nitrogen to aluminum of 0.88; and water to aluminum (5.24). Surface area was 20 $m^2$/gram. X-ray diffraction showed one hydrotalcite-like phase with d(003) spacing shifted to 8.87 Å. The complete diffraction pattern is summarized in Table B. The formula for this material was then computed to be: $Mg_{0.68}Al_{0.32}(OH)_2(CO_3^{-2})_{0.02}(NO_3^{-1})_{0.28} \cdot 0.69H_2O$.

TABLE B

Powder diffraction pattern of hydrotalcite-like material synthesized in Example 13

| d spacing (Å) | Relative Intensity |
|---|---|
| 8.87 | 100 |
| 4.46 | 66.2 |
| 2.59 | 14.0 |
| 2.35 | 12.1 |
| 2.06 | 6.0 |
| 1.52 | 17.0 |
| 1.51 | 12.0 |

EXAMPLE 14

A 500 milliliter portion of the same Example 12 slurry and 500 milliliters of distilled water were placed in a beaker with a continuous purge of nitrogen gas. A solution of sulfuric acid (12.0 milliliters added to 150 milliliters of distilled water) was added dropwise to the aforesaid until a pH of approximately 8.0 was reached. The sulfuric acid addition was 12.42 grams and the equilibrium pH measured at 7.71. This slurry was vacuum filtered and the solids dried overnight in a vacuum oven at 100° C. The solids weight was 68.8 grams. An analysis of these solids showed molar ratios of: magnesium to aluminum (2.13); carbon to aluminum (0.044); sulfur to aluminum (0.139); and water to aluminum (6.62). Surface area was 10 m$^2$/gram. X-ray diffraction showed only a hydrotalcite-like phase with d(003) spacing shifted to 8.74 Å. The complete diffraction pattern is shown in Table C. The formula for this material was computed to be: $Mg_{0.68}Al_{0.32}(OH)_2(CO_3^{-2})_{0.01}(SO_4^{-2})_{0.12}(OH^{-1})_{0.06} \cdot 1.08H_2O$.

TABLE C

Powder diffraction pattern of hydrotalcite-like material synthesized in Example 14

| d spacing (Å) | Relative Intensity |
| --- | --- |
| 8.74 | 100 |
| 4.38 | 61.4 |
| 2.59 | 5.5 |
| 2.37 | 5.0 |
| 2.06 | 2.6 |
| 1.52 | 7.4 |
| 1.51 | 4.5 |

EXAMPLE 15

A 500 milliliter portion of slurry from Example 12 and 100 milliliters of distilled water were placed in a beaker with a continuous purge of nitrogen gas. A solution of acetic acid (25.8 milliliters added to 150 milliliters of distilled water) was added dropwise thereto until a pH of approximately 8.0 was reached. The acetic acid addition was 15.48 grams and the equilibrium pH was 8.06. This slurry was vacuum filtered and the solids dried overnight in a vacuum oven at 100° C. The solids weight was 60.9 grams. An analysis of these solids showed molar ratios of: magnesium to aluminum (2.22); carbon to aluminum (2.25); water to aluminum (10.38). Surface area was measured at 2.4 m$^2$/gram. X-ray diffraction showed as many as three hydrotalcite-like phases with d(003) spacings shifted to approximately 11.7, 10.7 and 9.10 Å. The diffraction pattern of the predominant material is shown in Table D. From the foregoing, the formula for this compound was computed to be: $Mg_{0.69}Al_{0.31}(OH)_2(CH_3COO^{-1})_{0.35} \cdot 1.70H_2O$.

TABLE D

Powder diffraction pattern of hydrotalcite-like material synthesized in Example 15

| d spacing (Å) | Relative Intensity |
| --- | --- |
| 10.67 | 100 |
| 6.05 | 13.6 |
| 4.23 | 51.9 |
| 2.57 | 39.3 |
| 2.32 | 28.9 |
| 1.95 | 23.0 |
| 1.52 | 52.8 |

EXAMPLE 16

A 500 milliliter portion of slurry from Example 12 and 500 milliliters of distilled water were placed in a beaker with a continuous purge of nitrogen gas and succinic acid powder was added in small increments thereto until reaching approximately 8.0 pH. The succinic acid addition was 17.71 grams and the equilibrium pH was 8.16. This slurry was vacuum filtered and the solids dried overnight in a vacuum oven at 100° C. The solids weight was 70.8 grams. The analysis of these solids showed molar ratios of: magnesium to aluminum (2.14); carbon to aluminum (2.45); and water to aluminum (8.18). Surface area was 7.6 m$^2$/gram. X-ray diffraction showed only one hydrotalcite-like phase with d(003) spacing shifted to 8.80 Å. The complete diffraction pattern is shown in Table E. The formula for this material was computed to be: $Mg_{0.68}Al_{0.32}(OH)_2((CH_2)_2(COO)_2^{-2})_{0.19} \cdot 1.20H_2O$.

TABLE E

Powder diffraction pattern of hydrotalcite-like material synthesized in Example 16

| d spacing (Å) | Relative Intensity |
| --- | --- |
| 8.80 | 100 |
| 4.46 | 48.7 |
| 2.57 | 4.9 |
| 2.37 | 5.9 |
| 2.06 | 4.3 |
| 1.52 | 7.6 |
| 1.51 | 4.9 |

EXAMPLE 17

A 500 milliliter portion of slurry from Example 12 and 600 milliliters of distilled water were placed in a beaker with a continuous purge of nitrogen gas. Terephthalic acid powder was added to the above in small increments until a pH of approximately 8.0 was reached. The terephthalic acid addition was 24.92 grams and the equilibrium pH was 8.05. This slurry was vacuum filtered and the solids dried overnight in a vacuum oven at 100° C. The solids weight was 78.9 grams. An analysis of these solids showed molar ratios of: magnesium to aluminum (2.28); carbon to aluminum (4.68); and water to aluminum (10.42). Surface area was 30 m$^2$/gram. X-ray diffraction showed: a minor residual amount of terephthalic acid; the initial hydrotalcite-like material from Example 12 with d(003) spacing at 7.57 Å; and a hydrotalcite-like phase with d(003) spacing shifted to 11.45 Å. The diffraction pattern for the later phase is shown in Table F.

TABLE F

Powder diffraction pattern of hydrotalcite-like material synthesized in Example 17

| d spacing (Å) | Relative Intensity |
|---|---|
| 11.45 | 100 |
| 4.55 | 91.0 |
| 2.61 | 33.6 |
| 2.37 | 16.5 |
| 2.01 | 6.1 |
| 1.52 | 30.6 |
| 1.49 | 6.6 |

EXAMPLE 18

A 500 milliliter portion of slurry from Example 12 and 500 milliliters of distilled water were placed in a beaker with a continuous purge of nitrogen gas. Benzoic acid powder was added thereto in small increments until reaching approximately 8.0 pH. The benzoic acid addition was 31.54 grams and the equilibrium pH was 7.34. This slurry was vacuum filtered and the solids dried overnight in a vacuum oven at 100° C. The solids weight was 85.6 grams. An analysis of the solids showed molar ratios of: magnesium to aluminum (2.29); carbon to aluminum (6.70); and water to aluminum (12.87). Surface area was 37 $m^2$/gram. X-ray diffraction showed a hydrotalcite-like phase with d(003) spacing shifted to 7.70 Å, and no trace of residual benzoic acid. The diffraction pattern for this hydrotalcite-like phase is shown in Table G. The formula was computed to be: $Mg_{0.70}Al_{0.30}(OH)_2(C_6H_5COO^{-1})_{0.29} \cdot 2.18H_2O$.

TABLE G

Powder diffraction pattern of hydrotalcite-like material synthesized in Example 18

| d spacing (Å) | Relative Intensity |
|---|---|
| 7.70 | 100 |
| 3.85 | 67.9 |
| 2.57 | 15.0 |
| 2.40 | 2.6 |
| 1.93 | 1.4 |
| 1.52 | 11.9 |
| 1.49 | 2.5 |

EXAMPLE 19

A 500 milliliter portion of the Example 12 slurry and 400 milliliters of distilled water were placed in a beaker with a continuous purge of nitrogen gas. 25 grams of ammonium molybdate, $(NH_4)_6Mo_7O_{24} \cdot 4H_2O$ was added to the slurry and heated to 55°–60° C. for 5 hours to evolve ammonia. The equilibrium pH was 7.34. This slurry was vacuum filtered and the solids dried overnight in a vacuum oven at 100° C. The solids weight was 75.7 grams. An analysis of these solids showed molar ratios of: magnesium to aluminum (2.21); molybdenum to aluminum (0.481); carbon to aluminum (0.05); nitrogen to aluminum (0.040); and water to aluminum (6.70). Surface area was 2.1 $m^2$/gram. X-ray diffraction showed no residual ammonium molybdate and a hydrotalcite-like phase with d(003) spacing shifted to 9.23 Å. The diffraction pattern for the later phase is shown in Table H. The formula was computed to be: $Mg_{0.69}Al_{0.31}(OH)_2(MoO_4^{-2})_{0.15}(CO_3^{-2})_{0.015} \cdot 1.09H_2O$.

TABLE H

Powder diffraction pattern of hydrotalcite-like material synthesized in Example 19

| d spacing (Å) | Relative Intensity |
|---|---|
| 9.23 | 59.7 |
| 4.63 | 100 |
| 2.56 | 18.0 |
| 2.34 | 12.0 |
| 1.93 | 7.7 |
| 1.52 | 12.4 |
| 1.50 | 4.7 |

EXAMPLE 20

A 500 milliliter portion of slurry from Example 12 and 400 milliliters of distilled water were placed in a beaker with a continuous purge of nitrogen gas. 25 grams of ammonium tungstate, $(NH_4)_{10}W_{12}O_{41} \cdot 5H_2O$, was added to that slurry and heated to 55°–60° C. for 5 hours to evolve ammonia. The equilibrium pH was 10.70. This slurry was vacuum filtered and the solids dried overnight in a vacuum oven at 100° C. The solids weight was 83.7 grams. An analysis of these solids showed molar ratios of: magnesium to aluminum (2.38); tungsten to aluminum (0.448); carbon to aluminum (0.06); nitrogen to aluminum (0.06); and water to aluminum (7.36). Surface area was 18.8 $m^2$/gram. X-ray diffraction showed: no residual ammonium tungstate; small amounts of the initial hydrotalcite-like material from Example 12 with d(003) spacing at 7.79 Å; and a hydrotalcite-like phase with d(003) spacing shifted to 10.05 Å. The diffraction pattern for the later phase is shown in Table I. The compound's formula was computed to be: $Mg_{0.70}Al_{0.30}(OH)_2(WO_4^{-2})_{0.13}(CO_3^{-2})_{0.016} \cdot 1.17H_2O$.

TABLE I

Powder diffraction pattern of hydrotalcite-like material synthesized in Example 20

| d spacing (Å) | Relative Intensity |
|---|---|
| 10.05 | 22.7 |
| 4.83 | 100 |
| 2.57 | 37.3 |
| 2.30 | 30.7 |
| 1.93 | 38.7 |
| 1.52 | 42.7 |
| 1.49 | 13.3 |

EXAMPLE 21

A 500 milliliter portion of slurry from Example 12 and 200 milliliters of distilled water were placed in a beaker with a continuous purge of nitrogen gas. 30 grams of ammonium vanadate, $NH_4VO_3 \cdot 5H_2O$, was added to the slurry and heated to 55°–60 C. for 5 hours to evolve ammonia. The equilibrium pH was 8.47. This slurry was vacuum filtered and the solids dried overnight in a vacuum oven at 100° C. The solids weight was 80.6 grams. An analysis of these solids showed molar ratios of: magnesium to aluminum (2.28); vanadium to aluminum (0.92); carbon to aluminum (0.04); nitrogen to aluminum (0.05); and water to aluminum (6.02). Surface area was 15.6 $m^2$/gram. X-ray diffraction showed no residual ammonium vanadate, and a hydrotalcite-like phase with d(003) spacing shifted to 9.30 Å. The diffraction pattern for the later phase is shown in Table J. The formula therefor was computed to be: $Mg_{0.69}Al_{0.31}(OH)_2(VO_3^{-1})_{0.28}(CO_3^{-2})_{0.012} \cdot 0.839H_2O$.

TABLE J

Powder diffraction pattern of hydrotalcite-like material synthesized in Example 21

| d spacing (Å) | Relative Intensity |
| --- | --- |
| 9.30 | 55.8 |
| 4.68 | 100 |
| 2.59 | 37.3 |
| 2.30 | 30.7 |
| 1.93 | 38.7 |
| 1.52 | 42.7 |
| 1.49 | 13.3 |

Having described the presently preferred embodiments, it is to be understood that the invention may be otherwise embodied within the scope of the appended claims.

What is claimed is:

1. A method for making a layered double hydroxide with at least one dicarboxylate or polycarboxylate anion intercalated therein, said layered double hydroxide having the formula: $A_{1-x}B_x(OH)_2C_z \cdot mH_2O$, where A represents a divalent metal cation, B represents a trivalent metal cation, C represents a mono- to polyvalent anion, and x, z and m satisfy the following conditions: $0.09 < x < 0.67$; $z = x/n$, where n = the charge on the anion; and $2 > m > 0.5$, said method comprising:

(a) reacting at least one divalent metal compound and at least one trivalent metal oxide powder in an aqueous suspension to form a double hydroxide intermediate containing said divalent metal and said trivalent metal;

(b) contacting the double hydroxide intermediate with a divalent or polyvalent organic anion to make an intercalated layered double hydroxide; and (c) separating said intercalated layered double hydroxide from the suspension.

2. The method of claim 1 wherein the divalent metal cation A of said layered double hydroxide is selected from the group consisting of: $Mg^{2+}$, $Ni^{2+}$, $Cu^{2+}$, $Ca^{2+}$, $Fe^{2+}$, $Co^{2+}$, $Sn^{2+}$, $Mn^{2+}$, $Cr^{2+}$, $Cd^{2+}$, $V^{2+}$ and $Zn^{2+}$.

3. The method of claim 1 wherein the divalent metal compound of step (a) is selected from the group consisting of: a magnesium oxide, hydroxide or carbonate; a nickel oxide or carbonate; a copper oxide or carbonate; a calcium oxide-containing compound; an iron (II) oxide-containing compound; a cobalt oxide-containing containing compound; a tin oxide-containing compound; a manganese oxide-containing compound; a chromium oxide-containing compound; a cadmium oxide-containing compound; a vanadium oxide-containing compound; a zinc oxide-containing compound and mixtures thereof.

4. The method of claim 1 wherein the divalent metal compound of step (a) is selected from the group consisting of: a magnesium oxide, hydroxide or carbonatea zinc oxide-containing compound; a copper oxide or carbonate; a nickel oxide or carbonate; an iron (II) oxide-containing compound; a calcium oxide-containing compound; a manganese oxide-containing compound and mixtures thereof.

5. The method of claim 1 wherein the divalent metal compound of step (a) consists essentially of a magnesium oxide, hydroxide, carbonate or mixtures thereof.

6. The method of claim 1 wherein the divalent metal compound of step (a) is a powder selected from the group consisting of: basic magnesium carbonate, magnesium oxide, hydromagnesite and mixtures thereof.

7. The method of claim 6 wherein the powdered divalent metal compound consists essentially of hydromagnesite.

8. The method of claim 1 wherein the trivalent metal cation B of said layered double hydroxide is selected from the group consisting of: $Al^{3+}$, $Fe^{3+}$, $Ga^{3+}$, $Co^{3+}$, $Mn^{3+}$, $Sc^{3+}$, and $Cr^{3+}$.

9. The method of claim 1 wherein the trivalent metal oxide powder of step (a) is selected from the group consisting of: an aluminum oxide-containing compound; an iron (III) oxide-containing compound; a gallium oxide-containing compound; a cobalt (III) oxide-containing compound; a manganese oxide-containing compound; a scandium oxide-containing compound; a chromium oxide-containing compound and mixtures thereof.

10. The method of claim 1 wherein the trivalent metal oxide powder of step (a) is a powder selected from the group consisting of: an aluminum oxide-containing compound, an iron oxide-containing compound, a chromium oxide-containing compound and mixtures thereof.

11. The method of claim 1 wherein the trivalent metal oxide powder of step (a) consists essentially of a transition alumina.

12. The method of claim 11 wherein the transition alumina consists essentially of a rehydratable alumina powder.

13. The method of claim 11 wherein the transition alumina consists essentially of an activated alumina having a BET surface area of about 100 $m^2/g$ or greater.

14. The method of claim 1 wherein the divalent or polyvalent organic anion is represented by the formula $(RCOO^-)_x$, wherein $x = 2$ and R is selected from the group consisting of: hydrogen, an alkyl compound having from 1–30 carbons, a substituted alkyl compound, an alkenyl compound having from 2–30 carbons, a substituted alkenyl compound, an aryl compound having from 6–30 carbons and a substituted aryl compound.

15. The method of claim 1 wherein the divalent or polyvalent organic anion consists essentially of: an alkyl compound or a substituted alkyl compound.

16. The method of claim 15 wherein the divalent or polyvalent organic anion is a substituted alkyl compound having a substituent selected from the group consisting of: a halo, hydroxyl, nitro, amino, sulfonyl, keto, sulfo, sulfono, sulfuryl, phosphonyl, phosphono and aryl.

17. The method of claim 1 wherein the divalent or polyvalent organic anion consists essentially of: an alkenyl compound or a substituted alkenyl compound.

18. The method of claim 17 wherein the divalent or polyvalent organic anion is a substituted alkenyl compound having a substituent selected from the group consisting of: a halo, hydroxyl, nitro, amino, sulfonyl, keto, sulfo, sulfono, sulfuryl, phosphonyl, phosphono and aryl.

19. The method of claim 1 wherein the divalent or polyvalent organic anion consists essentially of: an aryl compound or a substituted aryl compound.

20. The method of claim 19 wherein the divalent or polyvalent organic anion is a substituted aryl compound having a substituent selected from the group consisting of: a halo, hydroxyl, nitro, amino, sulfonyl, keto, sulfo, sulfono, sulfuryl, phosphonyl, phosphono and aryl.

21. The method of claim 1 wherein the divalent or polyvalent organic anion is selected from the group consisting of: an oxalate, a malonate, a succinate, a glutarate, an adipate, a pimelate, a suberate, a sebacate, a decandioate, a dodecandioate, a maleate, a fumarate, a tartrate, a citrate, a phthalate, an isophthalate, a terephthalate, a 1,2,3-propanetricarboxylate, a hemimellitate, a 1,8-naphthalate, a pyromellitate, a diphenate, a saccharate, a tetrabromophthalate and mixtures thereof.

22. The method of claim 1 wherein the divalent or polyvalent organic anion consists essentially of an oxalate.

23. The method of claim 1 wherein the divalent or polyvalent organic anion consists essentially of a succinate.

24. The method of claim 1 wherein the divalent or polyvalent organic anion consists essentially of a terephthalate.

25. A method for making a divalent or polyvalent organic anion-intercalated hydrotalcite-like material, said method comprising:

(a) reacting a magnesium-containing powder and a transition alumina powder in an aqueous suspension to form a meixnerite intermediate;

(b) contacting the meixnerite intermediate with a dicarboxylate or polycarboxylate anion to make a hydrotalcite-like material; and (c) separating the intercalated hydrotalcite-like material from the suspension.

26. The method of claim 25 wherein the magnesium-containing powder is selected from the group consisting of: basic magnesium carbonate, magnesium oxide, hydromagnesite and mixtures thereof.

27. The method of claim 25 wherein the magnesium-containing powder consists essentially of hydromagnesite.

28. The method of claim 25 wherein the magnesium-containing powder consists essentially of activated magnesium oxide.

29. The method of claim 25 wherein the transition alumina consists essentially of a rehydratable alumina powder.

30. The method of claim 25 wherein the transition alumina consists essentially of an activated alumina having a B.E.T. surface area of about 100 $m^2/g$ or greater.

31. The method of claim 25 wherein the divalent or polyvalent organic anion is selected from the group consisting of: an oxalate, a malonate, a succinate, a glutarate, an adipate, a pimelate, a suberate, a sebacate, a decandioate, a dodecandioate, a maleate, a fumarate, a tartrate, a citrate, a phthalate, an isophthalate, a terephthalate, a 1,2,3-propanetricarboxylate, a hemimellitate, a 1,8-naphthalate, a pyromellitate, a diphenate, a saccharate, a tetrabromophthalate and mixtures thereof.

32. The method of claim 25 wherein the divalent or polyvalent organic anion consists essentially of an oxalate.

33. The method of claim 25 wherein the dicarboxylate or polycarboxylate anion consists essentially of a succinate.

34. The method of claim 25 wherein the dicarboxylate or polycarboxylate anion consists essentially of a terephthalate.

35. A method for making an oxalate-containing, hydrotalcite-like compound comprises:

(a) reacting a magnesium-containing powder and a transition alumina powder in an aqueous suspension to form a meixnerite intermediate;

(b) contacting the meixnerite intermediate with an excess of oxalate ions to form an oxalate-containing, hydrotalcite-like compound; and (c) separating the hydrotalcite-like compound from the suspension.

36. A method for making a layered double hydroxide with at least one dicarboxylate or polycarboxylate anion intercalated therein, said method comprising:

(a) reacting meixnerite with a divalent or polyvalent organic anion to make an intercalated layered double hydroxide; and (b) separating said intercalated layered double hydroxide from the suspension.

37. The method of claim 36 wherein the divalent or polyvalent organic anion is represented by the formula $(RCOO^-)_x$, wherein $x=2$ and R is selected from the group consisting of: hydrogen, an alkyl compound having from 1–30 carbons, a substituted alkyl compound, an alkenyl compound having from 2–30 carbons, a substituted alkenyl compound, an aryl compound having from 6–30 carbons and a substituted aryl compound.

38. The method of claim 36 wherein the divalent or polyvalent organic anion consists essentially of: an alkyl compound or a substituted alkyl compound.

39. The method of claim 38 wherein the divalent or polyvalent organic anion is a substituted alkyl compound having a substituent selected from the group consisting of: a halo, hydroxyl, nitro, amino, sulfonyl, keto, sulfo, sulfono, sulfuryl, phosphonyl, phosphono and aryl.

40. The method of claim 36 wherein the divalent or polyvalent organic anion consists essentially of: an alkenyl compound or a substituted alkenyl compound.

41. The method of claim 40 wherein the divalent or polyvalent organic anion is a substituted alkenyl compound having a substituent selected from the group consisting of: a halo, hydroxyl, nitro, amino, sulfonyl, keto, sulfo, sulfono, sulfuryl, phosphonyl, phosphono and aryl.

42. The method of claim 36 wherein the divalent or polyvalent organic anion consists essentially of: an aryl compound or a substituted aryl compound.

43. The method of claim 42 wherein the divalent or polyvalent organic anion is a substituted aryl compound having a substituent selected from the group consisting of: a halo, hydroxyl, nitro, amino, sulfonyl, keto, sulfo, sulfono, sulfuryl, phosphonyl, phosphono and aryl.

44. The method of claim 36 wherein the divalent or polyvalent organic anion is selected from the group consisting of: an oxalate, a malonate, a succinate, a glutarate, an adipate, a pimelate, a suberate, a sebacate, a decandioate, a dodecandioate, a maleate, a fumarate, a tartrate, a citrate, a phthalate, an isophthalate, a terephthalate, a 1,2,3-propanetricarboxylate, a hemimellitate, a 1,8-naphthalate, a pyromellitate, a diphenate, a saccharate, a tetrabromophthalate and mixtures thereof.

45. The method of claim 36 wherein the divalent or polyvalent organic anion consists essentially of an oxalate.

46. The method of claim 36 wherein the divalent or polyvalent organic anion consists essentially of a succinate.

47. The method of claim 36 wherein the divalent or polyvalent organic anion consists essentially of a terephthalate.

* * * * *

UNITED STATES PATENT AND TRADEMARK OFFICE
CERTIFICATE OF CORRECTION

PATENT NO. : 5,578,286
DATED : November 26, 1996
INVENTOR(S) : Edward S. Martin et al.

It is certified that error appears in the above-indentified patent and that said Letters Patent is hereby corrected as shown below:

On title page, item [54] and col. 1, lines 1-4, In the title

Corrected Title Should Read:

Two Powder Synthesis of Hydrotalcite and Hydrotalcite-Like Compounds with Divalent or Polyvalent Organic Anions Signed and Sealed this First Day of April, 1997

BRUCE LEHMAN

*Attest:*

*Attesting Officer*  *Commissioner of Patents and Trademarks*